United States Patent
Crisanti (10) Patent No.: US 7,968,512 B2
(45) Date of Patent: Jun. 28, 2011

(54) CONJUGATES THAT CONTAIN THE HOMEODOMAIN OF ANTENNAPEDIA

(75) Inventor: Andrea Crisanti, London (GB)

(73) Assignee: Trojan Technologies Limited, London (GB)

( * ) Notice: Subject to any disclaimer, the term of this patent is extended or adjusted under 35 U.S.C. 154(b) by 1917 days.

(21) Appl. No.: 10/789,403

(22) Filed: Feb. 27, 2004

(65) Prior Publication Data

US 2008/0317773 A1 Dec. 25, 2008

Related U.S. Application Data

(63) Continuation of application No. 09/486,676, filed as application No. PCT/GB98/02628 on Sep. 2, 1998, now abandoned.

(30) Foreign Application Priority Data

Sep. 2, 1997 (GB) .................................. 9718609.2

(51) Int. Cl.
*C07K 14/00* (2006.01)
(52) U.S. Cl. ........................................ 514/1.1; 530/350
(58) Field of Classification Search .................... None
See application file for complete search history.

(56) References Cited

FOREIGN PATENT DOCUMENTS

WO WO 97/12912 4/1997

OTHER PUBLICATIONS

Saffman et I. 1994; A differential response element for the homeotics at the antennapedia P1 promoter of Drosophila. Proc. Natl. Acad. Sci. 91: 7420-7424.*
Perez et al. 1994; Rab3A and Rab3B carbosy-terminal peptides are both potent and specific inhibitors of prolactin release by rat cultured anterior pituitary cells. Mol. Endocrin. 8: 1278-1287.*
Prochiantz, A. "Getting hydrophilic compounds into cells: lessons from homeopeptides" *Current Opinion in Neurobiology*, 1996, pp. 629-634, vol. 6, No. 5.
Derossi, D. et al. "Cell internalization of the third helix of the antennapedia homeodomain is receptor-independent" *Journal of Biological Chemistry*, 1996, pp. 18188-18193, vol. 271, No. 30.
Schutze-Redelmeier, M-P et al. "Introduction of exogenous antigens into the MHC class I processing and presentation pathway by Drosophila antennapedia homeodomain primes cytotoxic T cells in vivo" *Journal of Immunology*, 1996, pp. 650-655, vol. 157, No. 2.
Bonfanti, M. et al. "p21 WAF1-derived peptides linked to an internalization peptide inhibit human cancer cell growth" *Cancer Research*, 1997, pp. 1442-1446, vol. 57.
Brugidou, J. et al. "The retro-inverso form of a homeobox-derived short peptide is rapidly internalised by cultured neurones: A new basis for an efficient intracellular delivery system" *Biochemical and Biophysical Research Communications*, 1995, pp. 685-693, vol. 214, No. 2.
Simmons, C.G. et al. (1997) "Synthesis and membrane permeability of pna-peptide conjugates" *Bioorganic & Medicinal Chemistry Letters*, 1997, pp. 3001-3006, vol. 7, No. 23.

* cited by examiner

*Primary Examiner* — Karen Cochrane Carlson
(74) *Attorney, Agent, or Firm* — DLA Piper LLP (US)

(57) ABSTRACT

The subject invention pertains to a conjugate comprising: (a) a first region comprising the homeodomain of antennapedia or a variant thereof; and (b) a second region not naturally associated with the first region. In one embodiment, the second region of the conjugate comprises a protein of at least 100 amino acids.

7 Claims, 1 Drawing Sheet

SEQUENCE LISTING

```
<160> NUMBER OF SEQ ID NOS: 12

<210> SEQ ID NO 1
<211> LENGTH: 60
<212> TYPE: PRT
<213> ORGANISM: Drosophila sp.

<400> SEQUENCE: 1

Arg Lys Arg Gly Arg Gln Thr Tyr Thr Arg Tyr Gln Thr Leu Glu Leu
1               5                   10                  15

Glu Lys Glu Phe His Phe Asn Arg Tyr Leu Thr Arg Arg Arg Arg Ile
            20                  25                  30

Glu Ile Ala His Ala Leu Cys Leu Thr Glu Arg Gln Ile Lys Ile Trp
        35                  40                  45

Phe Gln Asn Arg Arg Met Lys Trp Lys Lys Glu Asn
    50                  55                  60

<210> SEQ ID NO 2
<211> LENGTH: 8
<212> TYPE: PRT
<213> ORGANISM: Artificial Sequence
<220> FEATURE:
<223> OTHER INFORMATION: Six histidine tail fused to conjugate for
      purification

<400> SEQUENCE: 2

His His His His His His Gly Ser
1               5

<210> SEQ ID NO 3
<211> LENGTH: 16
<212> TYPE: PRT
<213> ORGANISM: Drosophila sp.

<400> SEQUENCE: 3

Arg Gln Ile Lys Ile Trp Phe Gln Asn Arg Arg Met Lys Trp Lys Lys
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Variant sequence of helix 3. Must have between
```

6 and 10 hydrophobic amino acids.
<220> FEATURE:
<221> NAME/KEY: MISC_FEATURE
<222> LOCATION: (1)..(5)
<223> OTHER INFORMATION: Can be any alpha-amino acid.
<220> FEATURE:
<221> NAME/KEY: MISC_FEATURE
<222> LOCATION: (7)..(16)
<223> OTHER INFORMATION: Can be any alpha-amino acid.

<400> SEQUENCE: 4

Xaa Xaa Xaa Xaa Xaa Trp Xaa Xaa Xaa Xaa Xaa Xaa Xaa Xaa Xaa Xaa
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Variant sequence of helix 3. Must have between
      6 and 10 hydrophobic amino acids.
<220> FEATURE:
<221> NAME/KEY: MISC_FEATURE
<222> LOCATION: (1)..(10)
<223> OTHER INFORMATION: Can be any alpha-amino acid.
<220> FEATURE:
<221> NAME/KEY: MISC_FEATURE
<222> LOCATION: (12)..(16)
<223> OTHER INFORMATION: Can be any alpha-amino acid.

<400> SEQUENCE: 5

Xaa Xaa Xaa Xaa Xaa Xaa Xaa Xaa Xaa Xaa Trp Xaa Xaa Xaa Xaa Xaa
1               5                   10                  15

<210> SEQ ID NO 6
<211> LENGTH: 35
<212> TYPE: PRT
<213> ORGANISM: Drosophila sp.

<400> SEQUENCE: 6

Leu Thr Arg Arg Arg Arg Ile Glu Ile Ala His Ala Leu Cys Leu Thr
1               5                   10                  15

Glu Arg Gln Ile Lys Ile Trp Phe Gln Asn Arg Arg Met Lys Trp Lys
            20                  25                  30

Lys Glu Asn
        35

<210> SEQ ID NO 7
<211> LENGTH: 35
<212> TYPE: PRT
<213> ORGANISM: Drosophila sp.

<400> SEQUENCE: 7

Leu Thr Arg Arg Arg Arg Ile Glu Ile Ala Tyr Ala Leu Cys Leu Thr
1               5                   10                  15

Glu Arg Gln Ile Lys Ile Trp Phe Ala Asn Arg Arg Met Lys Trp Lys
            20                  25                  30

Lys Glu Asn
        35

<210> SEQ ID NO 8
<211> LENGTH: 35
<212> TYPE: PRT
<213> ORGANISM: Drosophila sp.

<400> SEQUENCE: 8

Leu Thr Arg Arg Arg Arg Ile Glu Ile Ala His Ala Leu Cys Pro Pro

```
1               5                   10                  15
Glu Arg Gln Ile Lys Ile Trp Phe Gln Asn Arg Arg Met Lys Trp Lys
            20                  25                  30
Lys Glu Asn
        35

<210> SEQ ID NO 9
<211> LENGTH: 4
<212> TYPE: PRT
<213> ORGANISM: Artificial Sequence
<220> FEATURE:
<223> OTHER INFORMATION: Factor Xa cleavage sequence.

<400> SEQUENCE: 9

Ile Glu Gly Arg
1

<210> SEQ ID NO 10
<211> LENGTH: 5
<212> TYPE: PRT
<213> ORGANISM: Artificial Sequence
<220> FEATURE:
<223> OTHER INFORMATION: Enterokinase cleavage sequence.

<400> SEQUENCE: 10

Asp Asp Asp Asp Lys
1               5

<210> SEQ ID NO 11
<211> LENGTH: 5
<212> TYPE: PRT
<213> ORGANISM: Artificial Sequence
<220> FEATURE:
<223> OTHER INFORMATION: Thrombin cleavage sequence.

<400> SEQUENCE: 11

Leu Val Pro Arg Gly
1               5

<210> SEQ ID NO 12
<211> LENGTH: 17
<212> TYPE: DNA
<213> ORGANISM: Artificial Sequence
<220> FEATURE:
<223> OTHER INFORMATION: GAL4 DNA binding domain.

<400> SEQUENCE: 12
cggaggacag tcctccg                                                  17
```

CONJUGATES THAT CONTAIN THE HOMEODOMAIN OF ANTENNAPEDIA

CROSS-REFERENCE TO RELATED APPLICATION

This application is a continuation of U.S. application Ser. No. 09/486,676, filed Jun. 8, 2000 now abandoned, which is the national stage of international application No. PCT/GB98/02628, filed Sep. 2, 1998.

The present invention relates to a novel conjugate, particularly, but not exclusively, in the form of a fusion protein or protein/nucleic acid complex.

Gene therapy provides the potential to permanently cure selected genetic diseases. However, a major obstacle is the effective delivery of the gene or protein of interest to the target site. A variety of viral and non-viral vectors have been developed to deliver genes or gene products to various cells, tissues and organs by ex vivo or in vivo strategies. Among viral-based vectors, retroviruses, adenoviruses, adeno-associated viruses and herpes viruses have been most extensively studied. Among non-viral-based vectors, liposomes have been used to introduce plasmid DNA directly into animals. However, one of the main challenges of gene therapy remains the design of effective delivery systems.

The gene antennapedia (Antp) encodes a transcriptional factor that has been shown to control antero-posterior morphogenesis in *Drosophila* embryo. The protein sequence of antennapedia is characterised by the presence of a 60 amino acids motif (homeodomain) that binds to specific DNA target elements. Antennapedia homologues have been found in nearly all multicellular organisms and show a very high degree of amino acid sequence identity. The human and *drosophila* antennapedia proteins differ in the sequence of the homeodomain only for one conservative amino acid substitution.

It has been observed that antennapedia and its homeodomain are able to translocate across the cytoplasmic membrane of mammalian cells. The translocation does not depend on cell endocytosis and it has been reported that translocation occurs at both 4° C. and 37° C. Homeodomain synthetic peptides made of D amino acids are also able to cross the cytoplasmic membrane. This finding would rule out the possibility that Antp is translocated through a receptor mediated mechanism. This property has been exploited to vehiculate small viral sequences into the cytoplasm of cultured cells as well as to elicit an MHC class I restricted cytotoxic immune response against the nucleoprotein of the influenza virus. However, to date the homeodomain of Antp has only been used to transport small synthetic peptides. Schutze-Redelmeier M-P et al (1996) Introduction of Exogenous Antigens into the MHC Class I Processing and Presentation Pathway by *Drosophila* Antennapedia Homeodomain Primes Cytotoxic T Cells In Vivo. *The Journal of Immunology* 650-655 mentions that the homeodomain of the antennapedia molecule can be used to deliver up to 50 additional amino acids to the cytoplasm. Using 16 amino acids of the third helix they mention that fusion peptides containing up to 94 amino acids could be prepared, but this is not demonstrated. Further the thrust of the disclosure is only towards delivery of synthetic peptides.

We have now found that the homeodomain of Antp can be used to translocate proteins, including non-synthetic proteins. One of the key advantages of the present invention is that is can be used to translocate functional and regulatory proteins. This is surprising and very important, particularly for medical applications.

The ability to deliver the expression product of a gene of interest directly into a cell has wide applicability, particularly in the medical field. We have now also surprisingly found that the homeodomain is able to translocate nucleic acid. This is especially advantageous for gene therapy applications.

Thus according to one aspect of the present invention there is provided a conjugate comprising:

(a) a first region comprising the homeodomain of antennapedia or a variant thereof; and (b) a second region not naturally associated with the first region;

and wherein at least the first region is non-denatured.

According to one embodiment the first and second regions are associated via for example a disulfide bond, or the second region may comprise a nucleic acid binding domain, preferably further comprising nucleic acid. This embodiment may be seen as a protein/nucleic acid complex.

According to a further embodiment the conjugate is in the form of a fusion protein. In this embodiment, preferably the second region is a functional or regulatory protein, or an antigen.

According to a further aspect of the present invention there is provided a conjugate comprising:

(a) a first region comprising the homeodomain of antennapedia or a variant thereof operably linked to (b) a second region not naturally associated with the first region comprising a protein of at least 100 amino acids.

By "operably linked" we include that the first and second region are linked such that the second region is able to translocate a cell membrane.

Preferably the whole conjugate is non-denatured.

By non-denaturing we do not necessarily imply a specific non-denaturing step; although this may be the case.

Denaturation is the process by which the three-dimensional shape of the protein molecule is changed from its native state without rupture of peptide bonds. It can also include disulfide bond rupture or chemical modification of certain groups in the protein if these processes are also accompanied by changes in its overall three-dimensional structure.

We also do not exclude renatured proteins or nucleic acid in which the denatured protein or nucleic acid is returned to the conformation it maintained before denaturation. Reversible denaturation is generally brought about by disulfide reducing agents, and urea, for nucleic acid by heat and salts.

For the avoidance of doubt, by native state we mean the form in which the protein or nucleic acid occurs in the intact cell, its three-dimensional structure depending on formation of the appropriate hydrogen bonds.

Preferably the first region is at the amino terminal end of the second region.

According to another aspect of the present invention there is provided nucleic acid encoding the conjugate of the present invention.

According to another aspect of the present invention there is provided an expression vector comprising the nucleic acid of the present invention operably linked to a promoter.

According to yet another aspect of the present invention there is provided a host cell transformed with the expression vector of the present invention.

The development of an appropriate procedure for obtaining the conjugate from bacterial lysate was important. With conventional methods we found that exposure to denaturing reagents dramatically affect the translocation property of the Antp homeodomain. We also found that small changes in pH and differences in osmolarity affected its translocation property.

We have now found a general method for preparing the conjugate of the present invention, and in particular an appropriate procedure for purifying the first domain and fusion proteins from the bacterial lysate. This method allows conjugates to be obtained which will translocate a protein of at least 100 amino acids across the cell membrane.

Thus according to another aspect of the present invention there is provided a method for preparing a conjugate comprising:

(i) culturing the host cell according to the present invention under conditions which provide for the expression of the conjugate from the expression vector within the host cell; and (ii) recovering the conjugate, which recovery comprises fusing an amino acid tail to the conjugate, which tail is capable of binding to at least one substrate and not to another substrate, and wherein the conjugate is caused to bind via the tail to at least one substrate such that components of the host cell do not bind to this substrate; and the conjugate is contacted with the other substrate such that the conjugate is not bound and remaining components of the host cell are bound to the other substrate.

According to yet another aspect of the present invention there is provided a method for preparing a conjugate comprising:

(i) culturing a host cell, transformed with an expression vector comprising nucleic acid, operably linked to a promoter, encoding (a) a first region comprising the homeodomain of antennapedia or a mutant thereof; and (b) a second region not naturally associated with the first region comprising an amino acid sequence of at least 100 amino acids in length, under conditions which provide for expression of the conjugate from the expression vector within the host cell; and (ii) recovering the conjugate, which method comprises fusing an amino acid tail to the conjugate, which tail is capable of binding to at least one substrate and not to another substrate, and wherein the conjugate is caused to bind via the tail to at least one substrate such that components of the host cell do not bind to this substrate; and the conjugate is contacted with the other substrate such that the conjugate is not bound and remaining components of the host cell are bound to the other substrate.

According to a further aspect of the present invention there is provided a method of purifying a conjugate comprising fusing an amino acid tail to the conjugate, which tail is capable of binding to at least one substrate and not to another substrate, and wherein the conjugate is caused to bind via the tail to at least one substrate such that impurities do not bind to this substrate; and the conjugate is contacted with the other substrate such that the conjugate is not bound and remaining impurities are bound to the other substrate.

Thus in broad terms the present invention can be seen as the use of a tail attached to the conjugate which allows both positive and negative purification steps.

Preferably the amino acid tail is fused to the carboxy terminal end of the conjugate.

Preferably the amino acid tail comprises HHHHHHGS (SEQ ID NO. 2).

Preferably the substrate is a nickel column or an antibody with affinity for the amino acid tail.

According to a preferred embodiment the conjugate is consecutively contacted with two substrates with which it has affinity via the amino acid tail.

Thus preferably both the nickel column and antibody are used. They may be used in any order.

When the second region is a DNA binding domain, a complex with nucleic acid may be formed by mixing the conjugate formed in accordance with the invention with the nucleic acid.

Further aspects of the present invention include a conjugate prepared by the method of the present invention; a pharmaceutical composition comprising the conjugate of the present invention and the use of the conjugate of the present invention in the preparation of a medicament for the treatment of a disease or infection.

In accordance with the invention, standard molecular biology techniques may be used which are within the level of skill in the art. Such techniques are fully described in the literature. See for example: Sambrook et al (1989) Molecular Cloning; a laboratory manual; Hames and Glover (1985-1997) DNA Cloning: a practical approach, Volumes I-IV (second edition); Methods for the engineering of immunoglobulin genes are given in McCafferty et al (1996) "Antibody Engineering: A Practical Approach".

BRIEF DESCRIPTION OF THE DRAWINGS

Various preferred features and embodiments of the present invention will now be described by way of non-limiting example, and with reference to the accompanying drawings in which.

BRIEF DESCRIPTION OF THE SEQUENCES

SEQ ID NO. 1 is an amino acid sequence of a protein according to the present invention.

SEQ ID NO. 2 is an amino acid sequence of a six histidine tail fused to conjugate for purification as described in the present invention.

SEQ ID NO. 3 is an amino acid sequence of helix 3 of the Antp homeodomain.

SEQ ID NO. 4 is an amino acid sequences of a variant of helix 3 according to the present invention.

SEQ ID NO. 5 is an amino acid sequences of a variant of helix 3 according to the present invention.

Figure 1:
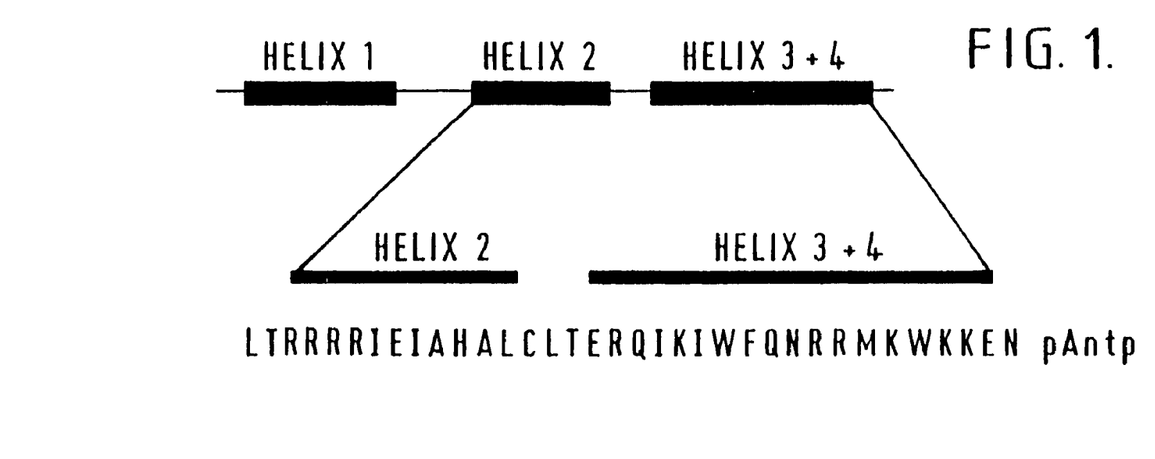
FIG. 1 shows the structure and sequence of the antennapedia homeodomain (SEQ ID NO. 6) obtainable from Drosophila.

SEQ ID NO. 6 is an amino acid sequence of helices 2, 3, and 4 of the Antp homeodomain as described in FIG. 1.

Figure 2:
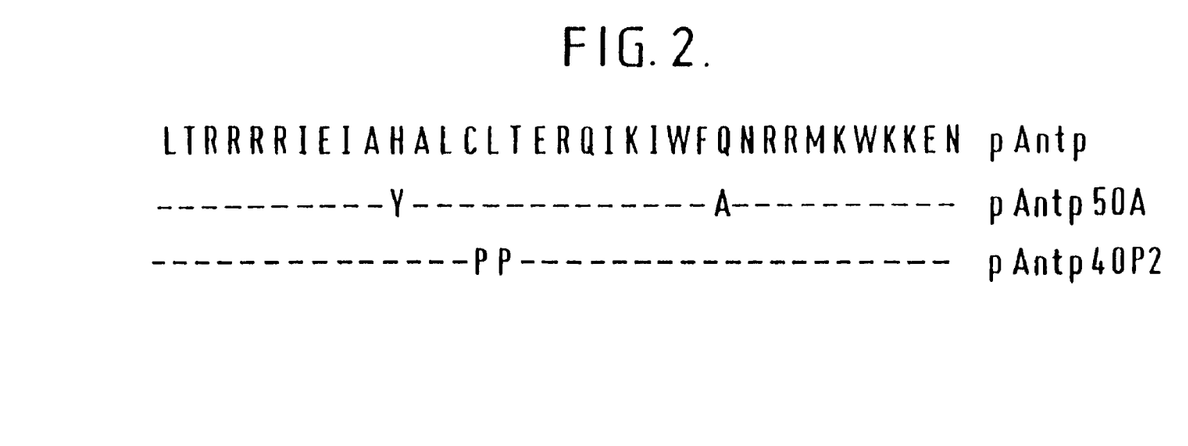
FIG. 2 further shows two mutants, designated pAntp 50H (SEQ ID NO. 7) and pAntp 40P2 (SEQ ID NO. 8).

SEQ ID NO. 7 is an amino acid sequence of a variant of SEQ ID NO. 6 as described in FIG. 2 as pAntp50A.

SEQ ID NO. 8 is an amino acid sequence of a variant of SEQ ID NO. 6 as described in FIG. 2 as pAntp 40P2.

SEQ ID NO. 9 is an amino acid sequence of the Factor Xa cleavage region.

SEQ ID NO. 10 is an amino acid sequence of the Enterokinase cleavage region.

SEQ ID NO. 11 is an amino acid sequence of the Thrombin cleavage region.

SEQ ID NO. 12 is an nucleotide sequence of the GAL4 DNA binding domain.

First Region

The first region of the conjugate of the invention may comprise a natural or synthetic homeodomain of antennapedia.

The homeodomain of the Antp gene obtainable from *Drosophila* is shown in FIG. 1 and in Seq ID No. 1. Sequences homologous to this homeodomain have been isolated from other organisms, including vertebrates, mammals and humans, and these are included in the present invention. The homeodomain may be prepared using standard techniques such as cloning using the procedure described in Joliet et al (1991) Antennapedia homeobox peptide regulates neural morphogenesis. *Proc. Natl. acad. Sci.* 88 1864-1868. As previously indicated differences in the sequences of such multicellular organisms are generally conservative in nature. However, this may not necessarily be the case and other such sequences are included in the present invention, and for example where the sequence identity is about 50% or more, e.g. 60%, 70%, 80% or 90%, with the sequence obtainable from *Drosophila*. Sequence identity may be determined using such commercially available programmes as GAP.

In addition synthetic variants may be used provided that they retain the ability to translocate the membrane. Synthetic variants will generally differ from the naturally-occurring proteins by substitution, particularly conservative substitution. By conservative amino acid changes we mean replacing an amino acid from one of the amino acid groups, namely hydrophobic, polar, acidic or basic, with an amino acid from within the same group. An example of such a change is the replacement of valine by methionine and vice versa. Other examples of conservative substitutions may be seen by reference to the following table:

| ALIPHATIC | Non-polar | G A P |
| | | I L V |
| | Polar - uncharged | C S T M |
| | | N Q |
| | Polar - charged | D E |
| | | R K |
| AROMATIC | | H F W Y |
| OTHER | | N Q D E |

Such variants may be prepared using standard recombinant DNA techniques such as site-directed mutagenesis. Where insertions are to be made, synthetic DNA encoding the insertion together with 5' and 3' flanking regions corresponding to the naturally-occurring sequence either side of the insertion site. The flanking regions will contain convenient restriction sites corresponding to sites in the naturally-occurring sequence so that the sequence may be cut with the appropriate enzyme(s) and the synthetic DNA ligated into the cut. The DNA is then expressed in accordance with the invention to make the encoded protein. These methods are only illustrative of the numerous standard techniques known in the art for manipulation of DNA sequences and other known techniques may also be used.

The ability of a naturally occurring or synthetic sequence to translocate the membrane may be tested by routine methods known in the art and illustrated in the accompanying examples.

Some variants of the homeodomain which retain the ability to translocate the membrane have been reported in the art and these are included in the scope of the present invention, together with any which become available.

For example, EP-B-0 485 578 to CNRS discloses homeopeptides comprising the helix 3 sequence of pAntp, and these are incorporated herein by reference.

WO97/12912 also to CNRS discloses the actual sequence of the helix 3 of pAntp, and variants thereof. These also are incorporated herein by reference. In particular, the 3 helix is said to have the sequence:

```
                                                  (SEQ ID NO. 3)
Arg-Gln-Ile-Lys-Ile-Trp-Phe-Gln-Asn-Arg-Arg-Met-
Lys-Trp-Lys-Lys
```

The variants are said to have the sequence:

```
                                                  (SEQ ID NO. 4)
X1-X2-X3-X4-X5-X6-X7-X8-X9-X10-X11-X12-X13-X14-
X15-X16
or
                                                  (SEQ ID NO. 5)
X16-X15-X14-X13-X12-X11-X10-X9-X8-X7-X6-X5-X4-X3-
X2-X1
``` wherein each X represents an α-amino acid, with X6 representing tryptophan; said peptide comprising between 6 and 10 hydrophobic amino acids.

Other variants are disclosed in for example, Gehring W (1987) Homeo Boxes in the Study of Development. *Science* 236 1245-1252 discloses a homeodomain of 62 amino acids, i.e. with glu at position 0 and lys at position 61. Bloch-Gallego E et al. (1993) Antennapedia Homeobox Peptide Enhances Growth and Branching of Embryonic Chicken Motoneurons In Vitro. *The Journal of Cell Biology* 120(2) 485-492 discloses a mutant called pAntp 40P2 (SEQ ID NO. 8) that was still able to translocate through the motoneuron membrane and to reach the nucleus. In this mutant the leucine and threonine residues in positions 40 and 41 were replaced by two proline residues. Le Roux et al. (1993). Neurotropic activity of the Antennapedia homeodomain depends on its specific DNA-binding properties. *Proc. Natl. Acad. Sci.* 90 9120-9124 discloses two mutants pAntp 50A (SEQ ID NO. 7) and pAntp 40P2 (SEC) ID NO. 8) as shown in FIG. 2 which retain the ability to translocate through the neuronal membrane. Schutze-Redelmeier M-P et al. (1996) supra disclose that a 16 amino acid C-terminal (third helix) segment has been used to address oligonucleotides and oligopeptides to the cytoplasm and nuclei of cells in culture.

However, whilst not wishing to be bound by any theory it is believed that for delivering the proteins of the present invention an amino acid sequence of about 60 is preferred.

Cleavable Linker Region

Preferably, the first and second regions are linked by a cleavable linker region this may be any region suitable for this purpose. Preferably, the cleavable linker region is a protease cleavable linker, although other linkers, cleavable for example by small molecules, may be used. These include Met-X sites, cleavable by cyanogen bromide, Asn-Gly, cleavable by hydroxylamine, Asp-Pro, cleavable by weak acid and Trp-X cleavable by, inter alia, NBS-skatole. Protease cleavage sites are preferred due to the milder cleavage conditions necessary and are found in, for example, factor Xa, thrombin and collagenase. Any of these may be used. The precise sequences are available in the art and the skilled person will have no difficulty in selecting a suitable cleavage site. By way of example, the protease cleavage region targeted by Factor Xa is I E G R (SEQ ID NO. 9). The protease cleavage region targeted by Enterokinase is D D D D K (SEQ ID NO. 10). The protease cleavage region targeted by Thrombin is L V P R G (SEQ ID NO. 11). Preferably the cleavable linker region is one which is targeted by endocellular proteases.

Second Region

Fusion Protein

The second region of the conjugate according to the invention may comprise any protein sequence of interest (hereinafter POI) which is not naturally associated with the first region. Usually this will mean that the POI will be found in nature encoded by a gene different from the gene encoding the first region. The second region may be from the same species as the first region, but are present in the conjugate of the invention in a manner different from the natural situation, or from a different species.

The second region of the present invention is preferably at least 100 amino acids in length. The present invention is particularly useful for longer sequences, e.g. at least 150, 200, 300, 400 or 1000 amino acids in length. For the avoidance of doubt the term "protein" as used herein also encompasses polypeptides of the required length; although by the term "polypeptide" we generally mean sequences of from 2 to 100 amino acids in length, usually 2 up to 60.

Protein/Nucleic Acid Complex

Within the present invention the nucleic acid comprises any nucleic acid of interest (hereinafter NOI), which may be e.g. therapeutically active or a reporter gene. The NOI may be DNA or RNA. In one embodiment the NOI is an oligonucleotide.

When the present invention relates to a protein/nucleic acid complex, the complex preferably further comprises a nucleic acid (or DNA) binding domain as part of the second region. The nucleic acid binding domain serves to mediate the specific, high affinity and non-covalent interaction of the protein component with the nucleic acid component.

The nucleic acid binding domain may be an RNA binding domain, or preferentially, a DNA binding domain, e.g. the DNA binding domain of a transcription factor, particularly a yeast or human transcription factor. Preferred is A GAL4 derivable domain, mediating the selective binding of the protein of the invention to the DNA sequence CGGAGGA-CAGTCCTCCG (SEQ ID NO. 12) (Cavey et al J Mol Biol 209:423, 1989). Most preferably the DNA binding domain consists of GAL4 amino acids 2 to 147. A DNA binding domain may bind to single-stranded or to a double stranded DNA on the second domain.

Another suitable domain would be a histone.

Applications for the conjugates of the present invention include (there may be overlap between these applications):

1. Antigen delivery system. An antigen is any agent that when introduced into an immunocompetent animal stimulates the production of a specific antibody or antibodies that can combine with the antigen. However, the antigen may need to be combined with a carrier to be able to stimulate antibody production. This is where the present invention comes in as it acts as a carrier by transporting the antigen from one side of the cell membrane to the other such that it can stimulate antibody production. By way of example, bacterial and viral antigens translocated by Antp in the cell cytoplasm may be processed and associated with MHC class I molecules. This antigen processing and presenting pathway is known to activate specific CD8 cytoxic lymphocytes.

2. Gene therapy. Gene therapy may include any one or more of: the addition, the replacement, the deletion, the supplementation, the manipulation etc. of one or more nucleotide sequences in, for example, one or more targeted sites—such as targeted cells. If the targeted sites are targeted cells, then the cells may be part of a tissue or an organ. General teachings on gene therapy may be found in Molecular Biology (Ed Robert Meyers, Pub VCH, such as pages 556-558).

By way of further example, gene therapy can also provide a means by which any one or more of: a nucleotide sequence, such as a gene, can be applied to replace or supplement a defective gene; a pathogenic nucleotide sequence, such as a gene, or expression product thereof can be eliminated; a nucleotide sequence, such as a gene, or expression product thereof, can be added or introduced in order, for example, to create a more favourable phenotype; a nucleotide sequence, such as a gene, or expression product thereof can be added or introduced, for example, for selection purposes (i.e. to select transformed cells and the like over non-transformed cells); cells can be manipulated at the molecular level to treat, cure or prevent disease conditions—such as cancer (Schmidt-Wolf and Schmidt-Wolf, 1994, Annals of Hematology 69; 273-279) or other disease conditions, such as immune, cardiovascular, neurological, inflammatory or infectious disorders; antigens can be manipulated and/or introduced to elicit an immune response, such as genetic vaccination. In a particularly preferred embodiment, Antp may be used to introduce functional proteins in the cytoplasm of genetically deficient cell types.

3. Cancer therapy. Antp may be used to transport into cancer cells molecules that are transcription factors and are able to restore cell cycle control or induce differentiation. For example it is understood that many cancer cells would undergo apoptosis if a functional P-53 molecule is introduced into their cytoplasm. The present invention may be used to deliver such gene products.

4. Develop antibacterial and antiviral measures. For example, Antp may be used to transport in the cytoplasm of infected cells recombinant antibodies or DNA binding molecules and which interfere with a crucial step of bacterial and viral replication.

We have now generated recombinant chimeric proteins constituted by the homeodomain of antennapedia fused either to the 85A antigen of *Mycobacterium tuberculosis* or to a single chain recombinant antibody directed against the malaria antigen Pb21.

5. Use in expression systems. For example, it is desirable to express exogenous proteins in eukaryotic cells so that they get processed correctly. However, many exogenous proteins are toxic to eukaryotic cells. In manufacturing exogenous proteins it is therefore desirable to achieve temporal expression of the exogenous protein. The system may therefore be used in connection with an inducible promoter for this or any other application involving such a system. In one such system, the loxP/cre system, the eukaryotic cell contains a gene encoding the protein of interest, functionally linked to a repressor. Thus, in the normal situation, the protein is not expressed. The Antp homeodomain may be fused to Cre recombinase which will excise the repressor gene. Application of this conjugate to the eukaryotic cell will thus cause expression of the protein.

6. Receptor-mediated signalling. A receptor is a cellular macromolecule that undergoes combination, with a hormone, neurotransmitter, drug or intracellular messenger to initiate a change in cell function. Receptors are concerned directly and specifically in chemical signalling between and within cells. By receptor-mediated we mean a response that requires the intermediary action of a receptor. Thus the present invention which is required to initiate a change in cell function.

7. Protein sorting.

8. DNA synthesis.

The invention is particularly important because it transports to the nuclei of cells, functional transcription factors which interfere with the endogenous expression of genes and/or which interfere with the process of viral or bacterial replication.

Suitable NOI coding sequences and POIs include those that are of therapeutic and/or diagnostic application such as, but are not limited to: sequences encoding or POs which are cytokines, chemokines, hormones, antibodies, engineered immunoglobulin-like molecules, a single chain antibody, conjugates, enzymes, immune co-stimulatory molecules, immunomodulatory molecules, anti-sense RNA, a trans-dominant negative mutant of a target protein, a toxin, such as endotoxin A, Colicin A, d-endotoxin, diphtheria toxin, *Bacillus* anthrox toxin, Cholera toxin, Pertussis toxin, *E. coli* toxins, Shigatoxin or a Shiga-like toxin, a conditional toxin, an antigen, a tumour suppressor protein and growth factors, membrane proteins, vasoactive proteins and peptides, antiviral proteins and ribozymes, and derivatives thereof (such as with an associated reporter group). When included, such coding sequences may be typically operatively linked to a suitable promoter, which may be a promoter driving expression of a ribozyme(s), or a different promoter or promoters.

The conjugate of the present invention may be used to deliver one or more NOI(s) or POI(s) useful in the treatment of the disorders listed in WO-A-98/05635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endoscierosis.

In addition, or in the alternative, the conjugate of the present invention may be used to deliver one or more NOI(s) or POI(s) useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration: inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as antimicrobials: modulators of e.g. metabolism or behaviour; as analgesics; treating specific deficiency disorders; in treatment of e.g. psoriasis, in human or veterinary medicine.

In addition, or in the alternative, the conjugate of the present invention may be used to deliver one or more NOI(s) or POI(s) useful in the treatment of disorders listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scieritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

The present invention also provides a pharmaceutical composition for treating an individual by gene therapy, wherein the composition comprises a therapeutically effective amount of the conjugate of the present invention. The pharmaceutical composition may be for human or animal usage. Typically, a physician will determine the actual dosage which will be most suitable for an individual subject and it will vary with the age, weight and response of the particular individual.

The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s), and other carrier agents that may aid or increase entry into the target site (such as for example a lipid delivery system).

Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

The delivery of one or more therapeutic genes or proteins according to the invention may be used alone or in combination with other treatments or components of the treatment. Diseases which may be treated include, but are not limited to: cancer, neurological diseases, inherited diseases, heart disease, stroke, arthritis, viral infections and diseases of the immune system. Suitable therapeutic genes include those coding for tumour suppressor proteins, enzymes, pro-drug activating enzymes, immunomodulatory molecules, antibodies, engineered immunoglobulin-like molecules, conjugates, hormones, membrane proteins, vasoactive proteins or peptides, cytokines, chemokines, anti-viral proteins, antisense RNA and ribozymes.

The conjugate may also contain one or more cytokine-encoding NOIs or cytokines. Suitable cytokines and growth factors include but are not limited to: ApoE, Apo-SAA, BDNF, Cardiotrophin-1, EGF, ENA-78, Eotaxin. Eotaxin-2. Exodus-2, FGF-acidic, FGF-basic, fibroblast growth factor-10 (Marshall 1998 Nature Biotechnology 16: 129). FLT3 ligand (Kimura et al. (1997), Fractalkine (CX3C), GDNF, G-CSF, GM-CSF, GF-β1, insulin, IFN-γ, IGF-I IGF-II, IL-1α, IL-1β, IL-2, IL-3. IL-4, IL-5, IL-6, IL-7, IL-8 (72 a.a.), IL-8 (77 a.a.), IL-9, IL-10, IL-11, IL-12, IL-13, IL-15, IL-16, IL-17, IL-18 (IGIF), Inhibin α, Inhibin β, IP-10, keratinocyte growth factor-2 (KGF-2), KGF, Leptin, LIF, Lymphotactin, Mullerian inhibitory substance, monocyte colony inhibitory factor, monocyte attractant protein (Marshall 1998 ibid), M-CSF, MDC (67 a.a.), MDC (69 a.a.), MCP-1 (MCAF), MCP-2, MCP-3, MCP4, MDC (67 a.a), MDC (69 a.a.), MIG, MIP-1α, MIP-1β, MIP-3α, MIP-3β, MIP4, myeloid progenitor inhibitor factor-1 (MPIF-1), NAP-2, Neurturin, Nerve growth factor, β-NGF, NT-3, NT-4, Oncostatin M, PDGF-AA, PDGF-AB, PDGF-BB, PF-4, RANTES, SDF1α, SDF1β, SCF, SCGF, stem cell factor (SCF), TARC, TGF-α, TGF-β, TGF-β2, TGF-β3, tumour necrosis factor (TNF), TNF-α, TNF-β, TNF-1, TPO, VEGF, GCP-2 GRO/IMGSA, GRO-β, GRO-γ, HCC1, 1-309, The conjugate of the present invention may comprise further suitable domains. These will be known to those skilled in the art. For example an endoplasmic reticulum retention signal functions to affect the intracellular routing of the internalized conjugate or protein/nucleic acid complex of the present invention. A suitable endoplasmic retention signal may be a mammalian endoplasmic reticulum retention signal.

Also present may be a translocation domain which serves to enhance nucleic acid or protein escape from the cellular vesicle system and thus to augment nucleic acid transfer by this route. This domain may serve to reduce or avoid lysomal degradation after internalization of the protein/nucleic acid into the target cell. Suitable translocation domains are derivable from toxins, particularly bacterial toxins, such as exotoxin A, Colicin A, d-endotoxin, diphtheria toxin, *Bacillus* anthrox toxin. Cholera toxin, Perrussis toxin, *E. coli* toxin toxins, Shigatoxin or Shiga-like toxin.

The first domain of the present invention may be modified to target cell sites other than the nucleus.

Additionally, or alternatively, also present may be a target cell-specific binding domain recognising a cell surface structure, such as a receptor protein or surface antigen on the target cell.

Nucleic Acids.

The invention also provides nucleic acid encoding the conjugates of the invention. These may be constructed using standard recombinant DNA methodologies. The nucleic acid may be RNA or DNA and is preferably DNA. Where it is RNA, manipulations may be performed via cDNA intermediates. Generally, a nucleic acid sequence encoding the first region will be prepared and suitable restriction sites provided at the 5' and/or 3' ends. Conveniently the sequence is manipulated in a standard laboratory vector, such as a plasmid vector based on pBR322 or pUC19 (see below). Reference may be made to Molecular Cloning by Sambrook et al. (Cold Spring Harbor, 1989) or similar standard reference books for exact details of the appropriate techniques.

Nucleic acid encoding the second region may likewise be provided in a similar vector system. Sources of nucleic acid may be ascertained by reference to published literature or databanks such as Genbank.

Nucleic acid encoding the desired first or second region may be obtained from academic or commercial sources where such sources are willing to provide the material or by synthesising or cloning the appropriate sequence where only the sequence data are available. Generally this may be done by reference to literature sources which describe the cloning of the gene in question.

Alternatively, where limited sequence data are available or where it is desired to express a nucleic acid homologous or otherwise related to a known nucleic acid, exemplary nucleic acids can be characterised as those nucleotide sequences which hybridise to the nucleic acid sequences known in the art.

Stringency of hybridisation refers to conditions under which polynucleic acids hybrids are stable. Such conditions are evident to those of ordinary skill in the field. As known to those of skill in the art, the stability of hybrids is reflected in the melting temperature (Tm) of the hybrid which decreases approximately 1 to 1.5° C. with every 1% decrease in sequence homology. In general, the stability of a hybrid is a function of sodium ion concentration and temperature. Typically, the hybridisation reaction is performed under conditions of higher stringency, followed by washes of varying stringency.

As used herein, high stringency refers to conditions that permit hybridisation of only those nucleic acid sequences that form stable hybrids in 1 M Na+ at 65-68° C. High stringency conditions can be provided, for example, by hybridisation in an aqueous solution containing 6×SSC, 5×Denhardt's, 1% SDS (sodium dodecyl sulphate), 0.1 Na+ pyrophosphate and 0.1 mg/ml denatured salmon sperm DNA as non specific competitor. Following hybridisation, high stringency washing may be done in several steps, with a final wash (about 30 min) at the hybridisation temperature in 0.2-0.1×SSC, 0.1% SDS.

Moderate stringency refers to conditions equivalent to hybridisation in the above described solution but at about 60-62° C. In that case the final wash is performed at the hybridisation temperature in 1×SSC, 0.1% SDS.

Low stringency refers to conditions equivalent to hybridisation in the above described solution at about 50-52° C. In that case, the final wash is performed at the hybridisation temperature in 2×SSC, 0.1% SDS.

It is understood that these conditions may be adapted and duplicated using a variety of buffers, e.g. formamide-based buffers, and temperatures. Denhardt's solution and SSC are well known to those of skill in the art as are other suitable hybridisation buffers (see, e.g. Sambrook, et al., eds. (1989) Molecular Cloning: A Laboratory Manual, Cold Spring Harbor Laboratory Press, New York or Ausubel, et al., eds. (1990) Current Protocols in Molecular Biology, John Wiley & Sons, Inc.). Optimal hybridisation conditions have to be determined empirically, as the length and the GC content of the probe also play a role.

Expression Vectors and Host Cells.

The nucleic acid encoding a conjugate according to the invention, or constituent part(s) thereof, can be incorporated into vectors for further manipulation. As used herein, vector (or plasmid) refers to discrete elements that are used to introduce heterologous DNA into cells for either expression or replication thereof. Selection and use of such vehicles are well within the skill of the artisan. Many vectors are available, and selection of appropriate vector will depend on the intended use of the vector, i.e. whether it is to be used for DNA amplification or for DNA expression, the size of the DNA to be inserted into the vector, and the host cell to be transformed with the vector. Each vector contains various components depending on its function (amplification of DNA or expression of DNA) and the host cell for which it is compatible. The vector components generally include, but are not limited to, one or more of the following: an origin of replication, one or more marker genes, an enhancer element, a promoter, a transcription termination sequence and a signal sequence.

Production of Antibodies.

Conjugates according to the invention may be used directly as immunogens, without the use of further adjuvants, to generate antisera and monoclonal antibodies.

In accordance with yet another embodiment of the present invention, there are provided antibodies specifically recognising and binding the conjugates according to the invention.

More preferably, however, the antibodies are specific for the second region of the conjugates, that is the polypeptide which is fused to the gene product of the invention in order to achieve expression thereof. Advantageously, the second region of the conjugate is recognised by the antibodies when in its natural context. Thus, where the second region is an isolated peptide or domain from a larger protein, that peptide or domain is recognised by the antibodies of the invention in the context of the whole of the larger protein.

The invention moreover provides a method for preparing an immunoglobulin, comprising the steps of.

a) immunising an animal with a conjugate according to the present invention: and b) recovering immunoglobulin specific for a region of the conjugate from the serum of the animal.

The antibodies (or immunoglobulins) may be isolated in the form of a crude preparation, i.e. an antiserum, by affinity chromatography against the conjugate.

Expression and Purification of Antp-Conjugates

Whilst not wishing to be bound by any theory we believe the ability of Antp-conjugates to translocate across the cell surface membrane may be very much dependent on the conformation of the recombinant proteins. We could not observe any translocation of the polypeptide by using either bacteria cell extracts or purified proteins exposed to small amounts of detergent (ionic and non-ionic) or denaturating agents (urea or guanidinuim). This conformation dependent property has represented a serious problem for using Antp-conjugates in both in vitro and in vivo experiments as all reports so far published use either synthetic peptides or bacterial cell extracts. We have overcome this limitation by purifying the Antp-conjugate under native conditions in accordance with the invention.

Example 1

We have introduced at the carboxyl-terminal end of the recombinant protein a tail of six histidine which confers to those proteins a high affinity for nickel ions. Bacteria cells expressing the recombinant proteins were lysed by repeated exposure to ultrasounds. Cell lysates were centrifuged and loaded on a nickel column (Quiagen). The protein bound to the column were eluted step wise by changing the pH of the buffer. Under these conditions the Antp-conjugates could be selectively enriched. We have estimated by gel electrophoresis that the Antp-conjugates contributed up to 75% of the material eluted from the nickel column in the pH range between 4.0 to 5.0. The Antp recombinant proteins were further purified by affinity chromatography using the antibody 4 D 11 directed against the histidine tail. The recombinant proteins were eluted from the column by changing the pH of the buffer. Our results indicate that fractions eluted at pH 2.8 contained the recombinant proteins nearly free of any bacterial contaminants. These protein fraction were then loaded on a polymixine column to selectively subtract LPS and related bacterial contaminants. Gel electrophoresis analysis indicated that the eluate of the polymixine column contained the recombinant protein devoid of bacterial contaminants (99.5% purity). Purified Antp-conjugates were tested for their ability to translocate across the cell surface membrane of different cell types. Our results indicate that the purified conjugates Antp-85A are able to translocate across a variety of cell lines (Hela, Hep-G2, P815 EL4) and human monocytes. The ability of Antp to vehiculate large molecules across the cell membrane was not affected by the particular amino-acid composition of the conjugates. A different Antp-fusion molecule, generated by using the malaria antigen Thrombospondin related anonymous protein (TRAP) of Plasmodium berghei of about 150 amino acids (Robson K J et al Mol Biochem Parasitol 1997; 84(1): 1-12), was translocated across the cell membrane as efficiently as the 85A constructs.

The Monoclonal Antibody 4 D11

The monoclonal antibody (mAb) 4 D 11 was found by screening in ELISA hybridomas generated from a mouse that was immunised with a recombinant protein containing a six histidine tail at its amino-terminal end. The antibody is available from Imperial College of Science, Technology and Medicine, Sherfield Building Exhbition Rd, London SW7 2AZ, UK c/o is Innovations Ltd, 47 Princes Gate, London SW7 2AZ, UK. A molecular characterisation of the epitope showed that this mAb recognises the amino acid sequence HHHHHHGS (SEQ ID NO. 2) both at the amino and at the carboxyl terminal end of recombinant proteins. The antibody has an IgG1 isotype and can be easily purified on protein A column. Our results indicate that 4 D 11 recognises the recombinant proteins containing the HHHHHHGS (SEQ ID NO. 2) in ELISA immunoblot, immuno-fluorescence. In addition purified 4 D 11 coupled to beads (affi-gel or CNBR activated sepharose) can be used to purify recombinant proteins under native conditions.

TBC Vaccine

The present invention may be used to provide a recombinant vaccine that is able to induce a humoral as well as a cell mediated helper and cytotoxic immune response against *M. tuberculosis* antigens. In order to elicit a MCH class I restricted cytotoxic immune response, the antigens employed in the vaccine should have access to the cytoplasmic compartment in the presenting cells of the immunised organism. The 85A protein is one of the member of the antigenic complex 85 ABC and represents the most abundant molecular species secreted *M. tuberculosis* in the culture media and during bacterial infection. Moreover, the protective immune response induced natural infection is mainly directed against the antigen 85A, this protein elicits the production of antibodies and cytokines and stimulate the cytotoxic T cells. This would reproduce the processing and presentation pathways occurring during the natural infection of *M. tuberculosis* and the immunisation procedures employing BCG. Whilst not wishing to be bound by theory, it is believed that the development of such a vaccine would require molecular vehicles for translocating bacterial proteins across the cell membrane into the cytoplasmic compartment.

Example 2

To demonstrate the possibility of using Antp as delivery system we have carried out the following experimental activities: (i) cloning of the 85A full length sequence in expression plasmids; (ii) development of synthetic genes encoding chimeric proteins in which the homeodomain of Ant has been inserted at the amino terminal end of the proteins 85A; (iii) expression in *E. coli* and purification of the recombinant proteins; (iv) development of a specific antiserum against 85A; and (v) analysis of the ability of Antp to vehiculate the mycobacterial polypeptides 85A into the cytoplasm of HeLa cell in culture.

A. Cloning of 85A Coding Sequence in the Expression Plasmid pDS56/RBSII

The full length 85A gene was amplified in PCR experiments using as template DNA extracted *M. tuberculosis* strain H37Rv. As primers for the PCR reaction we have used oligonucleotides deduced from the amino acid sequence of 85A. To facilitate cloning in the expression vectors the primer were designed to contain at their 5' end the restriction sites Bam HI and Sal I. The amplified sequence was cloned in the expression plasmid pDS56/RBSII thereby generating the plasmids pDS/85A. The amplified sequences 85A was sequenced to rule out the presence of mutations introduced during the amplification reaction. The expression unit of the plasmid pDS 56 RBSII is under the control of IPTG inducible promotor and yields conjugates containing a stretch of six histidines at their amino- or carboxyl-terminal end. The presence of the histidines confer to the proteins a high affinity for nickel ions. The recombinant protein 85A was expressed in *E. coli* and purified by affinity chromatography on nickel column. The yields and quality of the proteins recovered at the end of purification process were assessed by analysing the samples eluted from the affinity column with SDS acrylamide gel electrophoresis.

B. Development of Synthetic Genes Encoding the Chimeric Proteins Antp-85A

The sequence encoding the homeodomain of Antennapedia was amplified in PCR experiments using as template the DNA extracted from embryonic cells of *D. melanogaster*. The homeodomain encompasses the sequence of Antp from amino acid 297 to 356 and is encoded by a gene sequence that is not interrupted by introns.

As primers we have employed oligonucleotides deduced on the basis of the homeodomain sequences and containing the Bam HI restriction site at their 5' end. The PCR product was sequenced to rule out the presence of mutations introduced by PCR in the sequence of the homehodomain. The restriction site Bam HI allowed the cloning of the PCR product in the correct reading came in front of the sequence of 85A in the plasmid pDS/85A encoded the chimeric protein Antp-85A. This protein is characterised by the presence of the homeodomain of Antp and the hisidine tail at its amino- and carboxyl-terminal ends respectively. The sequence of Antp was introduced at the amino-terminal end to facilitate the correct folding of this domain in the context of chimeric protein sequences. The expression of the chimeric protein Antp-85A was assessed by analyising the bacterial lysate on SDS acrylamide gels. In immunoblot experiments the serum s-85A recognised molecules migrating with the molecular weight predicted for Antp-85A.

C. Functional Analysis of the Chimeric Proteins Antp-85A

To assess the ability of the chimeric protein to translocate across the cell membrane increasing amounts of purified Antp-85A were added to HeLa cells in culture. As control the cells were incubated with recombinant protein 85A that lacks the homeodomain of Antp at its amino-terminal end. After 3 hours of incubation at 37° C. the cells were fixed in formaldehyde and analysed with the antiserum s-85A to reveal the translocation of 85A epitopes into the cytoplasm. In immunofluorescence experiments the serum s-85A did not react with HeLa cells that were previously incubated with bacterial lysates containing 85A. This finding would indicate that these polypeptides are not able to cross the cell membrane. On the contrary the antiserum s-25 showed a clear cytoplasmic reactivity on HeLa cells that were incubated with the chimeric protein Antp-85A. This last result strongly indicated that the 85A epitopes were localised within the cytoplasm of cells incubated with Antp-85A thus indicating that the homeodomain of Antp has conferred to the chimeric proteins the ability to translocate across the superficial membrane. These findings all together would indicate that the strategy employed to vehiculate antigens into the cytoplasm across the cell membrane can be used to develop an experimental vaccine against tuberculosis. It is anticipated that the purified chimeric proteins Antp-85A may elicit in the immunised animals both a humoral and cell mediated helper and cytotoxic immune response.

Example 3

P/cre Regulated Expression of Proteins in Eukaryotic Cells

The Cre recombinase is a phage derived enzyme that cuts double strand DNA at specific sited (LoxP). When two of these sites are present in opposite orientation the intervening DNA sequence is excised. The Cre recombinase has been shown to work in distantly related organisms such as bacteria, yeast and mammalian cells. Antp may be used to deliver the Cre recombines inside the cell nucleus and for manipulating genomic DNA at precise locations in a temporal regulated manner. One of the possible applications of Antp-Cre fusion is the development off highly regulated systems for expressing genes in eukaryotic cells. Transformation vectors can be designed for expressing genes under the transcriptional control of a promotor containing, within two LoxP sites, DNA elements functioning as target sequences for transcription repressor factors. In the absence of Cre recombinase the presence of the repressor sequence would not allow the promotor to transcribe the genes cloned in the vector. By adding the Antp-Cre conjugate to cells the repressor sequence may be excised from the promotor thus allowing transcription to start. This type of expression vector may be extremely useful for studying the function of eukaryotic genes as well as for expressing biologically active molecule in large amounts.

Example 4

Control of Viral Expression by Antennapedia Delivery of Recombinant Transcription Factors We further investigate Antp delivery technology by assessing its ability to transport a functional form of the suppressive transcription factor Oct-2.4 into the nuclei of cultured cells. This factor is a member of the POU (Pit-Oct-Unc) family of transcription factors and originates from an alternative splicing of the Oct-2 gene transcript which only occurs in neuronal cells.

Oct-2.4 lacks the activation domain located at the C-terminal end of Oct-2 though it retains the ability to bind to the octamer DNA regulatory element AGTCAAT. In contrast to Oct-2, which acts as a positive regulatory factors on B lymphocytes promoters. Oct-2.4 can function as transcription repressor. Notably, Oct-2.4 was shown to suppress the transcription of the herpes simplex virus (HSV) immediate early (IE) genes by binding to an octamer related regulatory element in the IE genes promoter. Moreover, the ectopic expression of Oct 2.4 in HSV permissive cells down regulated the IE gene expression and inhibited the viral lytic cycle thus indicating that this factor may play an important function in determining the resistance of neuronal cells to HSV replication. Recombinant conjugates containing the homeodomain of Antp at the amino-terminal end of Oct-2.4 cross the cell surface membrane, reach the cell nuclei and down regulate the viral IE promoters.

This proposal has the objective to assess the ability of hAntp to transport Oct-2.4 across the surface membrane of living cells. To achieve this objective we: i) generate hAntp-Oct-2.4 fusion proteins; ii) assess the ability of the fusion proteins to bind to HSV IE promoters and to translocate across the cell membrane; iii) analyse the transcriptional activity of IE promoter constructs in cells treated with hAntp-Oct-2.4 fusion proteins. The experiments prove the feasibility of manipulating the expression of cellular and viral genes by using a non invasive protein delivery system and may lead to the development of a novel class of antiviral agents.

Methods

Development of hAntp-Oct-2.4 constructs: Oct-2.4 is amplified in PCR experiments using as template cDNA generated from human B lymphocytes mRNA. These cells have been previously shown to express the full length Oct-2 transcription factor. The Oct-2.4 PCR product is sequenced and used to generate constructs expressing recombinant proteins in E. Coli. The sequence encoding the homeodomain of Antp from amino acid 297 to 356 has been amplified from Drosophila DNA. This sequence has been modified by in situ mutagenesis to abolish its DNA binding properties and shown to translocate across the surface membrane of living cells. The hAntp sequence is cloned at the 5' end of the Oct-2.4 gene thus generating the construct hAntp-Oct-2.4 that will contain hAntp at the amino-terminal end of Oct-2.4. hAntp-Oct-2.4 has a molecular weight of about 40 kDa which falls within the size range of proteins translocated by the homeodomain of Antp. The functional properties of Oct-2.4 will not be affected by the insertion of the hAntp sequence. Structural analysis indicates that the suppressive and the DNA binding activity of Oct-2.4 are mediated by a 42 amino acid sequence (residues 141-182) and the POU domain respectively which both retain their function in different structural contexts as well as in chimeric proteins. We also generate the construct hAntp-ΔOct-2.4 which has been designed to encode a deleted Oct-2.4 factor encompassing the suppressive 42 amino acid sequence and the POU DNA binding domain. hAntp-ΔOct-2.4 will retain its suppressive transcriptional activity and translocate across the cell membrane more efficiently than hAntp-Oct-2.4 because of its reduced molecular size Expression of Oct-2.4 and hAntp-Oct-2.4 chimeric proteins in E. coli: hAntp-Oct-2.4, hAntp-ΔOct-2.4 and Oct-2.4 are expressed in E. coli using a vector that inserts a six histidine tail at their carboxyl-terminal ends. The presence of the His tail will allow the purification of the recombinant proteins by nickel chelate chromatography.

Experimental evidence indicates that proteins with this structural organisation are efficiently transported across the cell membrane.

To avoid the accumulation of incorrectly folded proteins we insert, at the amino-terminal end of hAntp-Oct-2.4, hAntp-ΔOct-2.4 and Oct-2.4 the signal sequence of Pel B which directs the secretion of recombinant proteins into the bacteria periplasm. This strategy has proven to be very convenient to recover functional heterologous proteins in E. coli. The expression of recombinant proteins in E. coli are assessed in immunoblot experiments by using the MAb 4D11 which recognises the histidine tail.

Membrane translocation and DNA binding property analysis: The DNA binding properties of the recombinant proteins hAntp-Oct-2.4, hAntp-ΔOct-2.4 and Oct-2.4 are assessed in gel retardation assays using oligonucleotides encompassing the natural and the related HSV octamer sequence. The specificity of the interaction will be investigated in competition assays using wild type and mutated octamer oligonucleotides. The hAntp-Oct-2.4 constructs are further investigated for their ability to cross the surface membrane of several cell lines including the BHK cells (ATCC: CRL-1632) which are susceptible to HSV infection and lack Oct-2 transcription factors. BHK cells are incubated with affinity purified hAntp-Oct-2.4, hAntp-ΔOct-2. Control experiments are carried out by incubating the cells with recombinant Oct-2.4 and unrelated hAntp-fusion proteins. The presence and the distribution of the recombinant constructs in the treated cells are analysed in immunofluorescence experiments. BHK cells incubated with hAntp-Oct-2.4, hAntp-ΔOct-2.4 and Oct-2.4 are fixed, permeabilised and processed for immunofluorescence using MAb 4 D 11.

Analysis of the transcriptional activity of hAntp-Oct-2.4 and hAntp-ΔOct-2.4: The suppressive transcriptional activity of hAntp-Oct-2.4 and hAntp-ΔOct-2 are assessed on BHK cells transformed with a HSV IE promoter reporter construct. A DNA sequence encompassing the IE gene 3 promoter from nucleotide −330 to +33 will be linked to the luciferase (Luc) gene in the transformation construct IE3-Luc. The selected DNA sequences contains the octamer related regulatory sequence TAATGARAT and is transcriptionally active in BHK cells. The IE3-Luc construct also contains a G418 resistance gene (neo) transcription unit consisting of: i) the MMTV-LTR retroviral promoter-ii) the neo gene- and iii) the SV40 splicing and polyadenylation sites. Transformed BHK cell clones are selected with geneticin (G418) and analysed by southern blot. Experimental evidence indicates that the HSV IE3 promoter will constitutively express high level of luciferase in IE3-Luc transformed BHK cells. To assess the ability of hAntp-Oct-2.4, hAntp-ΔOct-2.4 to suppress the transcriptional activity of the HSV IE3 promoter, IE3-Luc transformed BHK cells are cultured either in the absence or in the presence of different concentration of affinity purified hAntp chimeric proteins. As control the transformed cells are incubated with recombinant Oct-2.4 and unrelated hAntp fusion proteins. The transcriptional level of the HSV IE3 promoter are assessed by measuring the luciferase activity in BHK cell extracts collected at different time points after treatment. Functional hAntp-Oct-2.4, hAntp-ΔOct-2.4 chimeric protein translocated into the cell nucleus of IE3-Luc transformed BHK will significantly down regulate the baseline activity of the HSV IE3 promoter.

The relevance of the proposed experiments goes beyond the development a delivery system potentially able to interfere with the lytic cycle of HSV. The homeodomain of Antp has the ability to transport across the cell surface membrane a range of functional proteins of great biological and medical relevance.

I claim:

1. A conjugate comprising:
   (a) a first region comprising the homeodomain of antennapedia; and
   (b) a second region at the C-terminus of the first region and not naturally associated with the first region;
   wherein the second region comprises at least 100 amino acids, and wherein at least the first region is non-denatured.

2. The conjugate according to claim 1, in the form of a fusion protein.

3. The conjugate according to claim 1, wherein the second region is a functional or regulatory protein.

4. A pharmaceutical composition comprising the conjugate of claim 1, in combination with a pharmaceutically-acceptable carrier.

5. The pharmaceutical composition according to claim 4, in the form of a vaccine.

6. A conjugate prepared by a method comprising the steps:
   (i) culturing a host cell transformed with an expression vector comprising a nucleic acid encoding a conjugate according to claim 2 under conditions which provide for the expression of the conjugate within the host cell; and
   (ii) recovering the conjugate by affinity purification under non-denaturing conditions.

7. The conjugate prepared according to claim 6, wherein the conjugate comprises an amino acid tail that binds to an immobilised substrate.

* * * * *